(12) United States Patent
Lowry et al.

(10) Patent No.: US 7,337,129 B1
(45) Date of Patent: Feb. 26, 2008

(54) METHOD AND APPARATUS FOR ON-LINE PRESCRIPTION ORDERING

(75) Inventors: Ethan Lowry, Seattle, WA (US); David Sanderman, Redmond, WA (US)

(73) Assignee: Drugstore.com, Inc., Bellevue, WA (US)

( * ) Notice: Subject to any disclaimer, the term of this patent is extended or adjusted under 35 U.S.C. 154(b) by 0 days.

(21) Appl. No.: 09/478,936

(22) Filed: Jan. 6, 2000

(51) Int. Cl.
*G06Q 30/00* (2006.01)
(52) U.S. Cl. .......................................... 705/26; 705/37
(58) Field of Classification Search .................. 705/26, 705/27, 3, 37
See application file for complete search history.

(56) References Cited

U.S. PATENT DOCUMENTS 5,845,255 A * 12/1998 Mayaud ......................... 705/3

OTHER PUBLICATIONS

21CFR201.1, [Revised as of Apr. 1, 1999], downloaded from the Internet on Apr. 14, 2003, from www.access.gpo.gov/nara/cfr/wasiidx_99/21cfr201_99.html, 3 pages.*
FDA Center for Drug Evaluation and Research, Manual of Policies and Procedures, Table of Contents. Downloaded from the Internet Apr. 14, 2003, from www.fda.gov/cder/mapp.html, 9 pages.*
Chapter 5230.1, Availability of Labeling Guidances for Generic Drugs, CDER Manual of Policies and Procedures, MAPPs, downloaded from the Internet on Apr. 14, 2003 from www.fda.gov/cder/mapp/5230-1.pdf.*
Anonymous, "Entry-level system provides flexible service", Modern Materials Handling, Nov. 1998, vol. 53, Issue 13, p. 16, 7 pages, downloaded from the Internet on May 2, 2004.*

* cited by examiner

*Primary Examiner*—James Zurita
(74) *Attorney, Agent, or Firm*—Blakely, Sokoloff, Taylor & Zafman LLP

(57) ABSTRACT

Methods and apparatuses for on-line prescription ordering are described. A prescription order is placed via a World Wide Web site and stored in a database. A server device periodically searches the database for new prescription orders. New prescription orders are routed to a distribution center for processing. The appropriate medical data (e.g., age, medical condition) is also routed to the distribution center for use in filling the prescription. Insurance information is collected and processed, if necessary. In one embodiment, in certain situations, a "pre-fill" order is sent to the distribution center to cause the distribution center to determine the actual medication to be dispensed, the cost covered by the insurance and other prescription processing to occur. In response to a user making financial arrangements (e.g., providing a credit card number) to cover any costs not covered by the insurance the prescription is filled and is shipped to the appropriate individual.

16 Claims, 8 Drawing Sheets

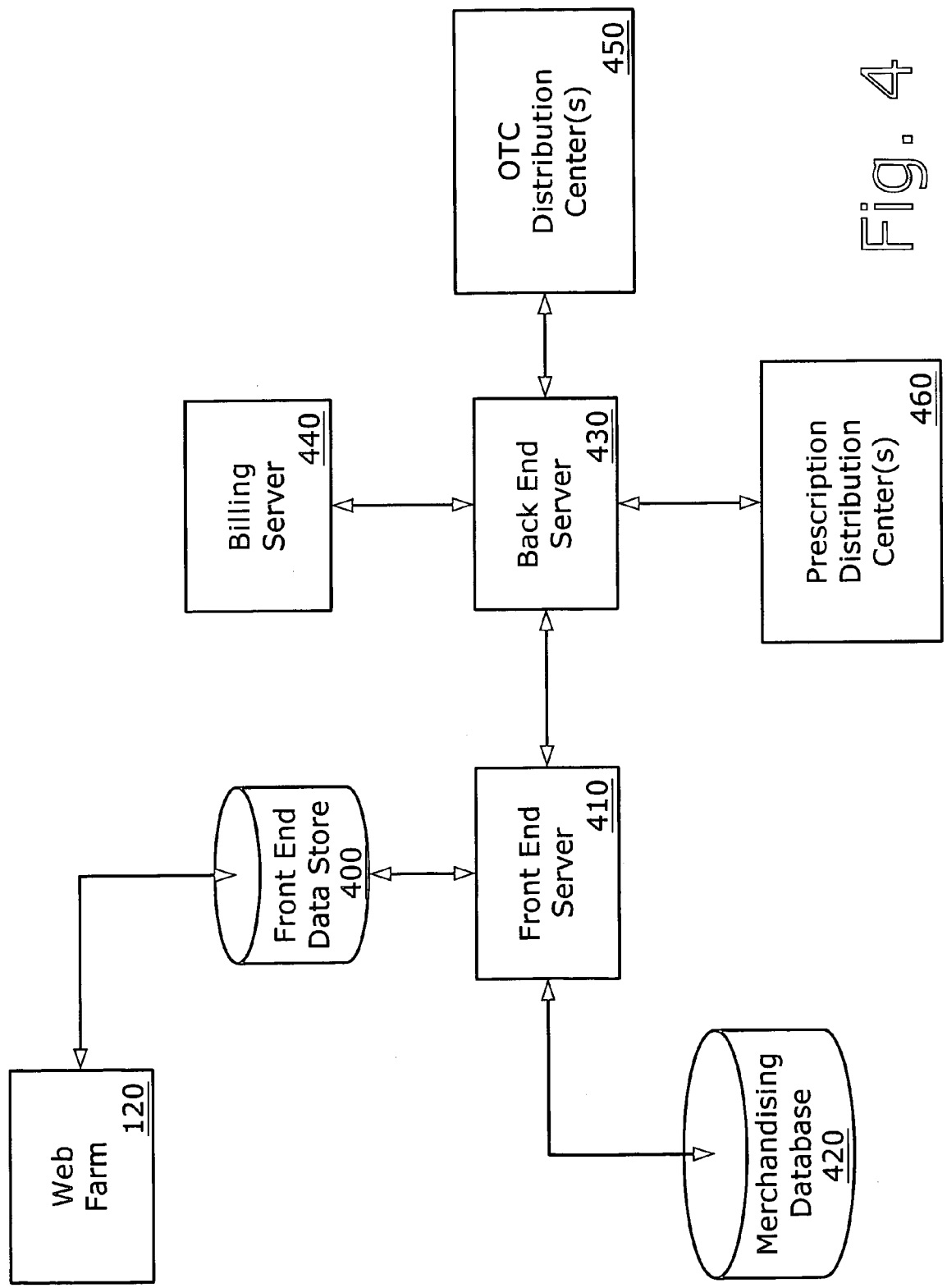

METHOD AND APPARATUS FOR ON-LINE PRESCRIPTION ORDERING

FIELD OF THE INVENTION

The invention relates to electronic commerce. More particularly, the invention relates to ordering prescription medications on-line.

BACKGROUND OF THE INVENTION

Typical prescription ordering is accomplished either by traveling to a specific pharmacy or mailing a prescription to a mail order pharmacy. Traditional prescription ordering is accomplished by an individual seeking to fill a prescription either taking a handwritten prescription to the pharmacy or having a doctor call a specific pharmacy and place the prescription over the phone. The individual then either waits for the prescription to be filled or travels to the pharmacy after the prescription is filled. This approach to filling prescriptions can be time consuming and frustrating.

For certain prescription medications, mail order prescription filling can be more convenient than filling the prescription at a pharmacy. Mail order prescription filling is typically used for prescriptions that are filled on a regular basis, for example, for long-term treatment for a particular medical condition. Mail order prescriptions can be convenient once established, but, generally, little information is available during the time that the prescription is being filled.

What is needed is an improved technique for filling prescriptions.

SUMMARY OF THE INVENTION

Methods and apparatuses for on-line prescription ordering are described. In one embodiment, the method includes receiving prescription order request. The prescription order request is forwarded to a distribution center. The distribution center is requested to acquire and to fill the prescription in response to the prescription order request and the distribution center acknowledging receipt of medical data used to process the prescription order. The distribution center provides an indication of a medication to be used to fill the prescription order and insurance information related to the prescription order. The distribution center is requested to ship the medication in response to receiving the indication of the medication to be used to fill the prescription order and the insurance information related to the prescription order.

BRIEF DESCRIPTION OF THE DRAWINGS

The invention is illustrated by way of example, and not by way of limitation in the figures of the accompanying drawings in which like reference numerals refer to similar elements.

FIG. 4 is one embodiment of an architecture for on-line prescription ordering.

DETAILED DESCRIPTION

Figure 1:
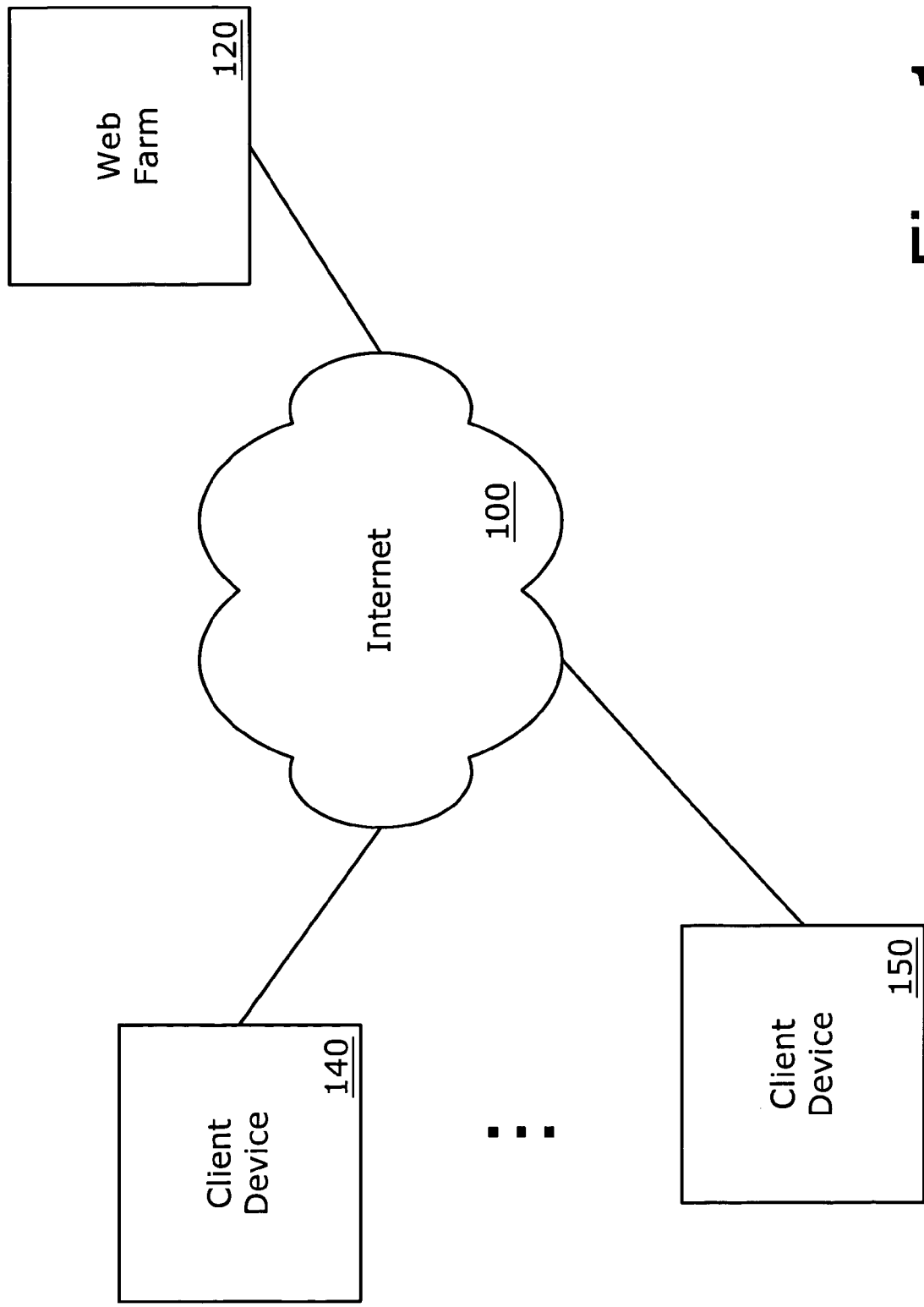
FIG. 1 is one embodiment of a network configuration for providing electronic commerce.

Methods and apparatuses for on-line prescription ordering are described. In the following description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

Methods and apparatuses for on-line prescription ordering are described. A prescription order is placed via a World Wide Web site and stored in a database. A server device periodically searches the database for new prescription orders. New prescription orders are routed to a distribution center for processing. The appropriate medical data (e.g., age, medical condition) is also routed to the distribution center for use in filling the prescription. Insurance information is collected and processed, if necessary. In one embodiment, in certain situations, a "pre-fill" order is sent to the distribution center to cause the distribution center to determine the actual medication to be dispensed, the cost covered by the insurance and other prescription processing to occur. In response to a user making financial arrangements (e.g., providing a credit card number) to cover any costs not covered by the insurance the prescription is filled and is shipped to the appropriate individual.

Electronic Commerce System Overview

FIG. 1 is one embodiment of a network configuration for providing electronic commerce. Internet 100 provides a global interconnection of computing devices. The configuration of FIG. 1 illustrates the Internet as an interconnection medium between various parties; however, any network configuration (e.g., local area network, wide area network, metropolitan area network, Internet, intranet), whether wired or wireless, can be used. Also, any appropriate networking protocol can be used.

Client device 140 and client device 150 represent devices used to access networked resources for a user of the respective client devices. Any number of client devices can be coupled to Internet 100. In one embodiment, client devices 140 and 150 are computer systems; however, other devices can also be used. For example, client devices 140 and/or 150 can be "set-top boxes" or "Internet terminals" such as a WebTV™ terminal available from Sony Electronics, Inc. of Park Ridge, N.J., or a set-top box using a cable modem to access a network such as the Internet.

Alternatively, client devices 140 and/or 150 can be "dumb" terminals or thin client devices such as the ThinSTAR™ available from Network Computing Devices, Inc. of Mountain View, Calif. In another alternative embodiment, client devices 140 and/or 150 can be hand held electronic devices, for example, personal digital assistants (PDAs), cellular telephones, pagers, or other electronic devices that provide network access.

Web farm 120 represents any configuration of servers that provide access to electronic resources such as, for example, Web pages, databases. In one embodiment Web farm 120 includes multiple Hypertext Markup Language (HTML) servers that provide electronic commerce Web pages to client devices 140 and/or 150. Any configuration that provides access to electronic resources using any appropriate protocol can be used.

Figure 2:
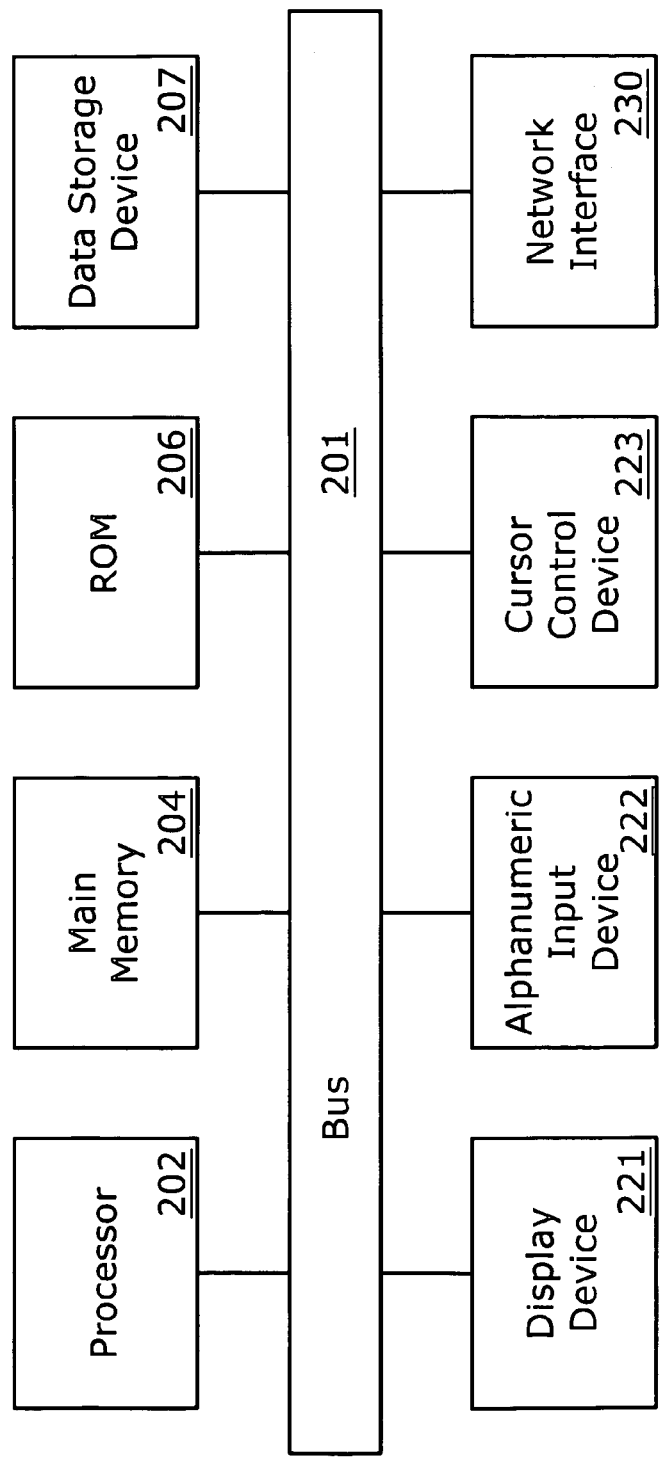
FIG. 2 is one embodiment of a computer system suitable for use with electronic commerce.

FIG. 2 is one embodiment of a computer system suitable for use with the invention. The computer system illustrated in FIG. 2 is intended to represent a range of computer systems. Alternative computer systems can include more, fewer and/or different components.

Computer system 200 includes bus 201 or other communication device to communicate information, and processor 202 coupled to bus 201 to process information. While computer system 200 is illustrated with a single processor, computer system 200 can include multiple processors and/or co-processors. Computer system 200 further includes random access memory (RAM) or other dynamic storage device 204 (referred to as main memory), coupled to bus 201 to store information and instructions to be executed by processor 202. Main memory 204 also can be used to store temporary variables or other intermediate information during execution of instructions by processor 202.

Computer system 200 also includes read only memory (ROM) and/or other static storage device 206 coupled to bus 201 to store static information and instructions for processor 202. Data storage device 207 is coupled to bus 201 to store information and instructions. Data storage device 207 such as a magnetic disk or optical disc and corresponding drive can be coupled to computer system 200.

Computer system 200 can also be coupled via bus 201 to display device 221, such as a cathode ray tube (CRT) or liquid crystal display (LCD), to display information to a computer user. Alphanumeric input device 222, including alphanumeric and other keys, is typically coupled to bus 201 to communicate information and command selections to processor 202. Another type of user input device is cursor control 223, such as a mouse, a trackball, or cursor direction keys to communicate direction information and command selections to processor 202 and to control cursor movement on display 221.

Network interface 230 provides an interface between computer system 200 and an external network (not shown in FIG. 2). Network interface 230 can be, for example, a network interface card (NIC) or any other type of network interface capable of providing network access to computer system 200.

In one embodiment, computer system 200 provides at least a portion of on-line prescription order processing in response to processor 202 executing sequences of instructions contained in main memory 204. Multiple computer systems, such as computer system 200, can be used. For example, a server device and a client device can both be computer systems.

Instructions are provided to main memory 204 from a storage device, such as magnetic disk, a read-only memory (ROM) integrated circuit (IC), CD-ROM, DVD, via a remote connection (e.g., over a network), etc. In alternative embodiments, hard-wired circuitry can be used in place of or in combination with software instructions to provide on-line prescription ordering. Thus, the on-line prescription ordering is not limited to any specific combination of hardware circuitry and software instructions.

Figure 3:
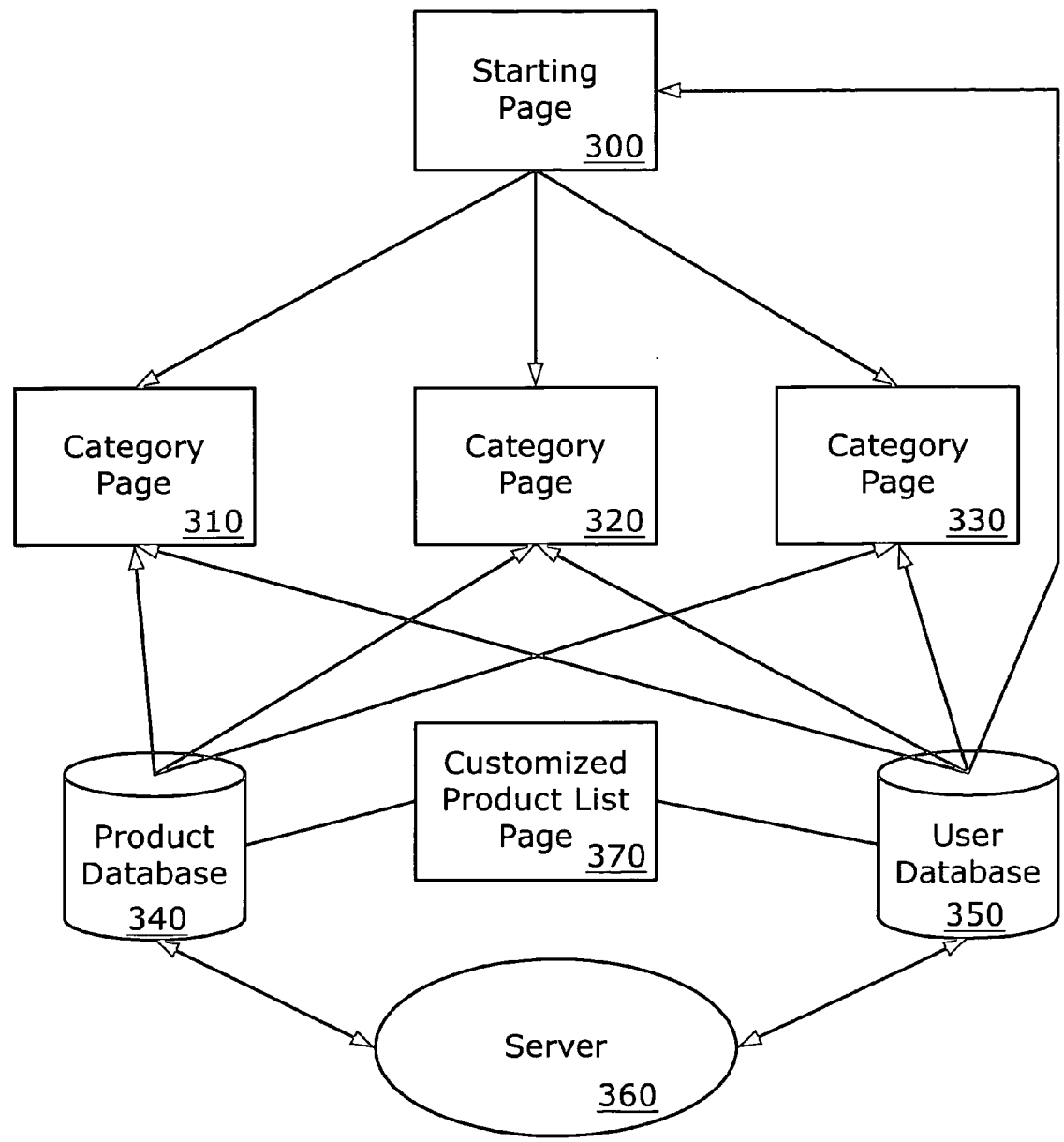
FIG. 3 illustrates one embodiment of a configuration for providing a set of World Wide Web electronic commerce pages.

FIG. 3 illustrates one embodiment of a configuration for providing a set of World Wide Web electronic commerce pages. Starting page 300 provides a starting page for users of an electronic commerce site. Starting page 300 can be different for different users to provide a more customized experience for the user or starting page 300 can be the same for all users. In one embodiment, starting page 300 is a Hypertext Markup Language (HTML) document; however, any appropriate programming language can be used.

Starting page 300 can receive user information from user database 350. In one embodiment, user database 350 stores information (e.g., name, address, preference information, previous order information) related to users of the electronic commerce site. User information can be retrieved from user database 350 based on, for example, using a "cookie" stored on the user's computer system to identify which user to retrieve information for, or alternatively, based on a login procedure.

In general, a cookie is information that a Web server stores on a client device to provide information to the server at a later time. A cookie can, for example, provide identification information, preferences, or similar information to the server when the client device subsequently contacts the server. The cookie can be used to identify a user and the corresponding information can be retrieved from user database 350 and used without requiring the user to enter information that had previously been provided.

From starting page 300, a user can navigate to one of several category pages (e.g., 310, 320, 330). In one embodiment, the category pages provide information (e.g., photographs, prices, manufacturer) related to various products offered for sale through the electronic commerce site. In one embodiment, product information is provided in response to user requests by product database 340, which can be implemented in any manner known in the art. Also, although not shown in FIG. 3, product database 340 can also provide information to starting page 300.

Category pages are not required; however, some organization of information that a user can navigate may provide a better experience for the user. Starting page 300 can also provide links to multiple related Web pages, rather than categories. For example, starting page 300 can operate as an electronic commerce "mall" and provide links to more specific electronic commerce sites (e.g., clothing, jewelry, electronics).

In one embodiment, user database 350 maintains a record of products previously purchased by various users as well as other useful information. In one embodiment, one more products previously purchased are presented to the user in the form of a list. The user can select a product from the list for simplified reordering or for other (e.g., research, pricing) information. The list can be presented in several formats with various categorizations. The following are some, but not all, of the formats and categorizations in which the list of products can be presented.

The list of products can be presented as a pull-down/pop-up menu, as a menu item, as a linked document, or in any other format. When the list of products is presented to the user, the list includes all of the products previously purchased, all of the products previously purchased within a predetermined time period, a predetermined number of products. The products included in the list can be categorized in any manner, selected categories of products can be presented, etc. Any other useful categorization can also be used.

The user can select one or more of the products from the list for reordering. In one embodiment, shipping information (e.g., address, shipping method, payment method) are verified in response to a product being selected and the server causes the product to be ordered and shipped to the user. If the shipping information has changed or is inaccurate, the user can modify the shipping information as needed.

In one embodiment, customized product list page 370 is compiled from product database 340 and user database 350 for each user that accesses starting page 300. Customized product list page 370 includes information related to previous purchases. For example, customized product list page 370 can list all products previously purchased by a particular user, either in a categorized (e.g., by product category, by date, by price) format or an uncategorized format. Customized product list page 370 can also include additional information such as, for example, products the user intends to purchase in the future, or products that the user wishes to research. A customized product listing can also be provided to the user in a different format, for example, the listing can be in the form of a menu or any other format.

Server 360 operates in conjunction with product database 340 and user database 350 to provide starting page 300 and multiple category pages with product information and user information as described above.

Prescription Ordering

FIG. 4 is one embodiment of an architecture for on-line prescription ordering. The architecture assumes a World Wide Web based electronic commerce site for ordering prescriptions. As described above, Web farm 120 includes one or more Web servers that provide the electronic commerce site. Any appropriate configuration can be used for Web farm 120.

Front end data store 400 provides and receives data from Web farm 120. In one embodiment, front end data store 400 stores four types of data: (1) catalog data, (2) pharmacy data, (3) user data, and (4) order data. In alternate embodiments, front end data store can store additional and/or different types of data. In one embodiment, servers included in Web farm 120 read and write data to front end data store 400, but the servers do not initiate processes on other devices.

Catalog data is data related to over-the-counter products available from the electronic commerce Web site and includes such information as, for example, categories to which the products belong, brand information for the products, ingredient lists, pricing information. The servers of Web farm 120 can read catalog data from front end data store 400 to provide product information to users of the electronic commerce Web site. In FIG. 3, catalog data is illustrated as stored in a separate database (product database 340); however, the catalog data can be stored in a separate database or a combined database.

Pharmacy data is data related to prescription products available from the electronic commerce Web site and includes such information as, for example, drug names, dosage information, overdoes information, missed dose information, pricing information. The servers of Web farm 120 can read the pharmacy data from front end data store 400 to provide prescription drug information to users of the electronic commerce Web site.

User data is data related to users of the electronic commerce Web site and can include information such as, for example, user name, password, patient information for individuals other than the user (e.g., spouse, child). In FIG. 3, user data is illustrated as a separate database (user database 350); however, the user data can be stored in a separate database or a combined database. The user data can be used for security, ordering, or other purposes.

Order data is related to current and/or past orders. In one embodiment, order data includes information related to pending orders, both prescription and non-prescription orders, as well as information related to orders place during a previous predetermined period of time (e.g., one year, six months). The order data can be used, for example, to allow a user to track a particular order electronically.

Front end server 410 communicates with front end data store 400 to process orders and to update catalog data and pharmacy data. In one embodiment, merchandising database 420 is used to maintain merchandising information such as, for example, purchase orders, inventory, and/or other information. Front end server 410 can use merchandising database 420 to update front end data store 400 so that Web farm 120 presents accurate information to users.

In one embodiment, front end server 410 periodically executes a batch process to search front end data store 400 for new orders. Front end server 410 analyzes the order data to determine whether new orders have been placed since the last batch has been run. New order data is copied from front end data store 400 and forwarded to back end server 430. One embodiment of order processing is described in greater detail below.

Back end server 430 operates with front end server 410 to process orders for both prescription and non-prescription products. In one embodiment, back end server 430 shields from end server 410 from slower communications links to various billing and/or distribution centers. In an alternate embodiment, the functionality of front end server 410 and back end server 430 can be combined.

Back end server 430 forwards billing information to billing server 440. Billing information can include, for example, credit card numbers, insurance information, user identification information, shipping and/or billing addresses, and/or any other useful information. Billing serer 440 performs billing operations based on the information provided by back end server 430. In one embodiment, billing server 440 contacts the appropriate credit card company to process a credit card payment.

In one embodiment, back end server 430 separates orders into prescription orders and non-prescription orders. Orders that include both prescription and non-prescription components are divided into one or more prescription sub-orders and non-application prescription sub-orders. In one embodiment, prescription orders and sub-orders are forwarded to prescription distribution center(s) 460, which represents one or more physical distribution facilities that ships prescription products. As described in greater detail below, prescription distribution center(s) 460 obtain information required to fill the prescription order. Non-prescription orders and sub-orders are forwarded to over-the-counter (OTC) distribution center(s) 450, which represents one or more physical distribution facilities that ships non-prescription products.

In one embodiment, communications to and from back end server 430 and between front end server 410 and merchandising database 420 are accomplished using a reliable, in-order, packetized messaging protocol. In one embodiment, communication is accomplished using Microsoft MessageQueue links; however, other protocols can also be used.

Figure 5A:
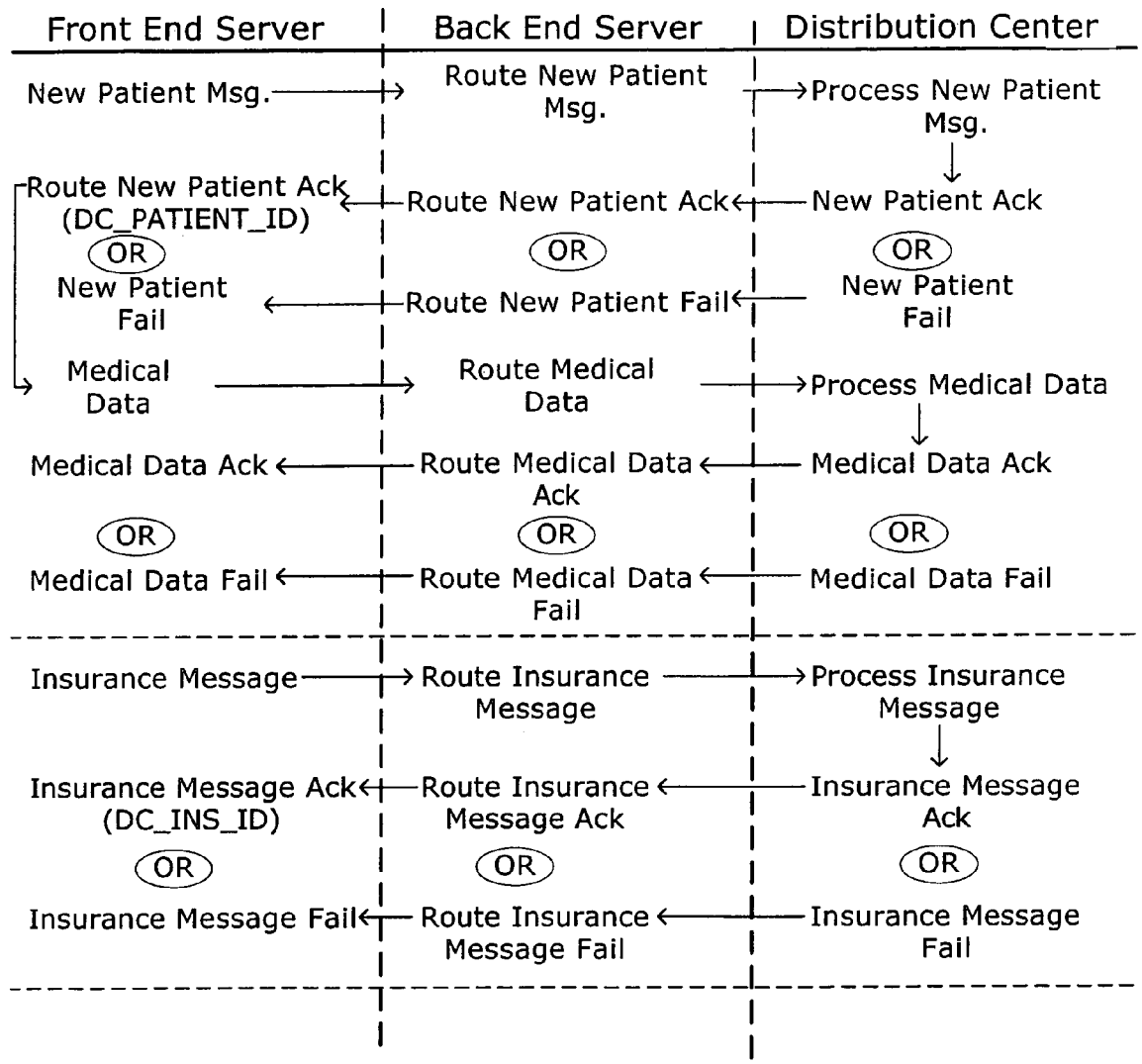
FIG. 5a and FIG. 5b are a conceptual illustration of one embodiment of a prescription ordering process.
Figure 5B:
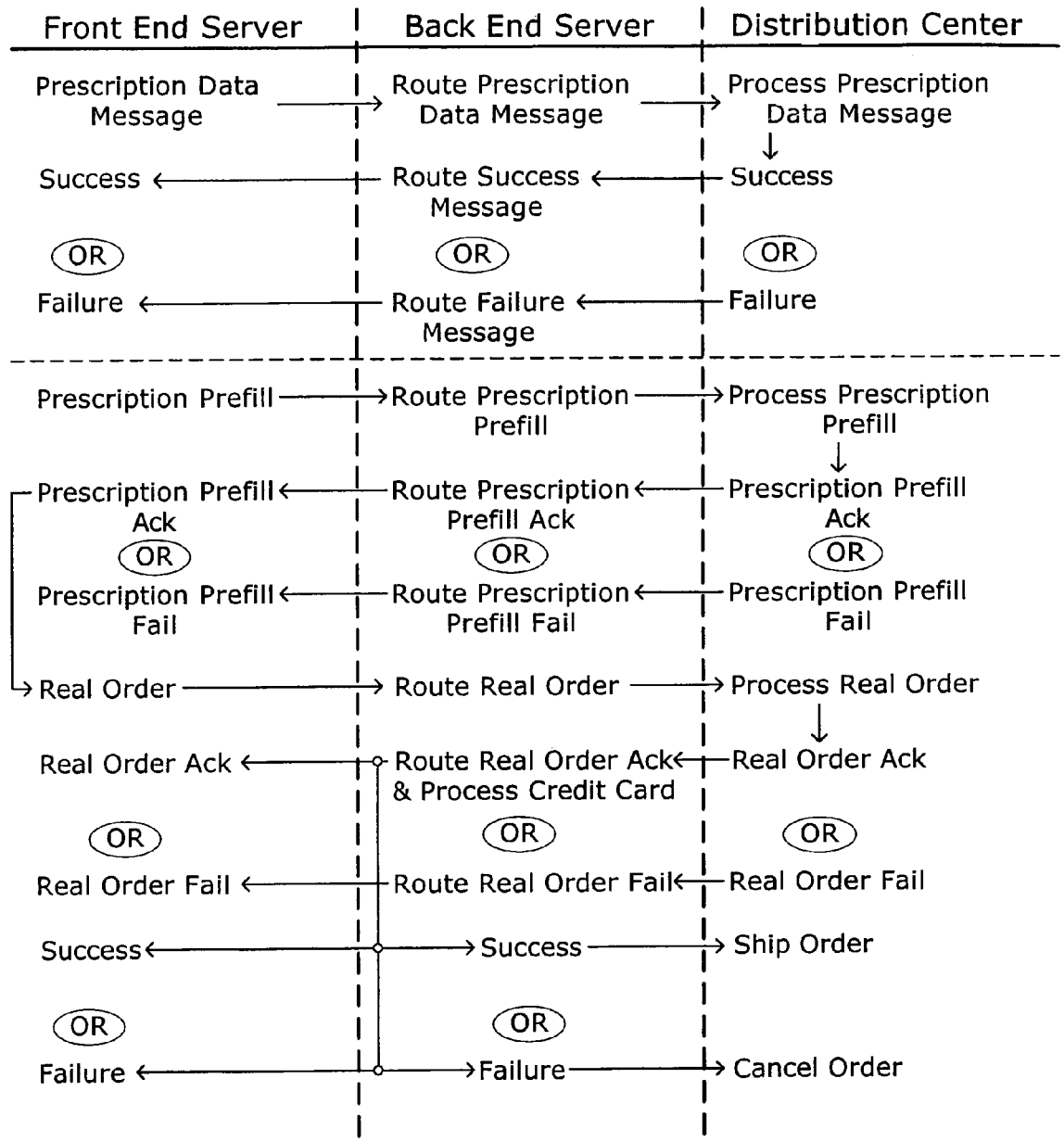

FIG. 5a and FIG. 5b are a conceptual illustration of one embodiment of a prescription ordering process. In one embodiment prescription ordering is processed by three devices: a front end server, a back end server, and a distribution center. In alternate embodiments, prescription ordering can be processed by different devices, for example, a front end server and a distribution center. In one embodiment, the message processing of FIG. 5a and FIG. 5b is accomplished using Microsoft MessageQueue links; however, other protocols can also be used.

The front end server generates a new patient message in response to a prescription order being placed. In one embodiment, a Web server writes a prescription order to a front end data store, and the front end server periodically polls the front end data store to determine whether new prescription orders have been placed. The new patient message is sent to the back end server, which routes the new patient message to an appropriate distribution center. In one embodiment, the distribution center is determined based on the shipping address associated with the prescription order, the geographical location of the distribution center and the inventory of the distribution center. The distribution center closest to the shipping address is selected.

The distribution center processes the new patient message and generates either a new patient acknowledge message or a new patient failure message. The new patient acknowledge message is generated if the distribution center successfully processes the new patient message. In one embodiment, the new patient acknowledge message includes a patient identifier (DC_PATIENT_ID) that is used in subsequent messages. The new patient failure message is generated if the distribution center cannot successfully process the new patient message because, for example, information is missing or incorrect. In one embodiment, the new patient failure message includes codes indication the reason for failure; however, failure codes are not necessary.

The new patient acknowledge message or new patient failure message is sent to the back end server, which routes the message to the front end server. The front end server takes the appropriate action in response to receiving the new patient acknowledge message or the new patient failure message. If the front end server receives the new patient failure message, the front end server notifies the party placing the prescription order that the order has failed. In one embodiment, information from the failure message is written to the front end data store by the front end server; however, notification can be provided in another manner (e.g. electronic mail message).

In response to the new patient acknowledge message, the front end server generates a medical data message including the patient identifier from the new patient acknowledge message. In one embodiment, the medical data message includes allergen information related to the patient, currently prescribed medications, and/or current medical condition. Other information can be provided in addition to, or rather than, this information. In one embodiment, each type of medical data (e.g., allergens, current condition, current medications) is processed using a separate medical data message; however, multiple types of data can be processed by a single medical data message.

The medical data message is sent to the back end server, which routes the medical data message to the appropriate distribution center. The distribution center processes the medical data message and generates a medical data acknowledge message or a medical data failure message. The medical data acknowledge message or the medical data failure message is sent to the back end server, which routes the message to the front end server.

In one embodiment, the new patient message processing and the medical data processing is referred to herein as patient data processing. In one embodiment, subsequent message processing assumes that the patient data processing has been accomplished and the patient identifier is used for subsequent processing. Patient data processing is performed prior to subsequent processing because proper pharmacy practice is to receive all relevant patient medical data prior to dispensing a prescription drug.

In response to successful patient data processing, the front end server generates an insurance message as part of insurance processing. The insurance processing is optional. In one embodiment, the insurance message includes the patient identifier. The insurance message includes insurance information (e.g., insurance carrier, plan number, group number) for the individual for which the prescription is placed.

In one embodiment, the insurance message includes insurance card information and relationship information. The insurance card information is the information used to determine insurance coverage (e.g., carrier name, card holder name, member ID, group number, plan name/number) and the relationship information indicates the relationship of the individual for which the prescription is placed to the card holder (e.g., self, spouse, child). The card information and the relationship information can be processed together or independently.

The insurance message is sent to the back end server, which routes the insurance message to the appropriate distribution center. The distribution center processes the insurance message and generates either an insurance acknowledge message or an insurance failure message. In one embodiment, the insurance failure message includes codes indicating the cause of the failure. In one embodiment, the insurance acknowledge message includes an insurance identifier (DC_INS_ID) that is used to identify insurance coverage for the associated prescription order.

The insurance acknowledge message or the insurance failure message is sent to the back end server, which routes the insurance acknowledge message or the insurance failure message to the front end server. In one embodiment, processing of the insurance message is accomplished before subsequent message processing is started; however, overlap of message processing can be supported.

In response to completion of the insurance message processing, the front end server generates a prescription data message. In one embodiment, the prescription data message includes information used for prescription processing (e.g., doctor name and/or phone number, pharmacy name and/or phone number, prescription number, transfer information). In one embodiment, the prescription data is free form text that is interpreted by a human operator; however, automated processing can also be supported. The prescription data can be used, for example, to acquire prescriptions from a pharmacy, a doctor's office, etc.

The prescription data message is sent to the back end server, which routes the prescription data message to the appropriate distribution center. The distribution center processes the prescription data message. In response, the distribution center generates a success or a failure message that is sent to the back end server. In one embodiment, the failure message includes failure codes that indicate the cause of the failure. In alternate embodiments, failure codes are not used.

In one embodiment, the success message includes a prescription number that is used to refer to the prescription in subsequent messages. The success message can also include additional information such as, for example, the National Drug Code, quantity information, refill information, prescription label information, dosage information, strength information, packaging information, pricing information, usage instructions, doctor name, number, and/or phone number. In one embodiment, the success message information is also stored in a prescription table for later use.

The success or failure message is forwarded to the front end server by the back end server. In response to a failure message, the front end server notifies the ordering party that a problem exists with the prescription order. In one embodiment, the front end server writes a failure notification to the front end data store, which is used to notify the ordering party; however, other notification schemes can also be used.

In one embodiment, in response to a success message, the front end server generates a "pre-fill" order to cause order processing to proceed prior to completion of the financial side of the transaction. The pre-fill procedure can be used to cause a drug utilization review, a substitution review, and/or an insurance adjudication.

The drug utilization review is a procedure in which the pharmacy analyzes the current medical condition of the individual receiving the prescription, the medical history of the person, any other drugs being used by the person and any other relevant factors to determine whether the prescribed drug is safe. The substitution review determines whether the person will receive a name brand medication or a generic equivalent of the name brand medication. The insurance adjudication causes the insurance company to determine benefits, which also determines the payment required from the person ordering the prescription medication. Adjudication can also result in substitution, and may require a doctor's authorization before allowing the prescription to be filled.

The prescription order is sent to the back end server, which forwards the prescription order to the distribution center. The distribution center processes the prescription order and generates a prescription order acknowledge message or a prescription order failure message. The prescription order acknowledge message or the prescription order failure message includes failure codes indicating the cause of the failure; however, failure codes are not necessary.

In one embodiment, the prescription order acknowledge message indicates the drug that will be dispensed (e.g., name brand or generic), the copay or payment amount required from the ordering party (if any) and any other appropriate information. The prescription order acknowledge or prescription order failure message is sent to the back end server, which forwards the prescription order acknowledge or prescription order failure message to the front end server.

In one embodiment, if the front end server receives a prescription order failure message, a notification is sent to the ordering party. In response to a prescription order acknowledge message, the front end server generates a real order message. The real order message is sent to the back end server, which routes the real order message to the appropriate distribution center. The distribution center processes the real order message and generates a real order acknowledge message or a real order failure message.

The real order acknowledge message or the real order failure message is sent to the back end server. If the back end server receives a real order failure message, the real order failure message is forwarded to the front end server and the front end server notifies the ordering party that the prescription cannot be filled. In one embodiment, the real order failure message includes a failure code that indicates the cause of the failure; however, the failure code is not necessary.

In one embodiment, when the back end server receives a real order acknowledge message, the back end server causes the ordering party's credit card to be charged for the prescription. In one embodiment, the back end server causes a billing server to process the credit card charge; however, any manner of processing credit card charges can be used.

If the credit card is charged successfully, the back end server generates a success message that is sent to the front end server and a ship order message that is sent to the distribution center. The distribution center ships the prescription order in response to the ship order message. If the credit card is not charged successfully, the back end server generates a failure message that is sent to the front end server and a cancel order message that is sent to the distribution center. The distribution center cancels the order in response to the cancel order message.

Automatic Product Listing

Figure 6:
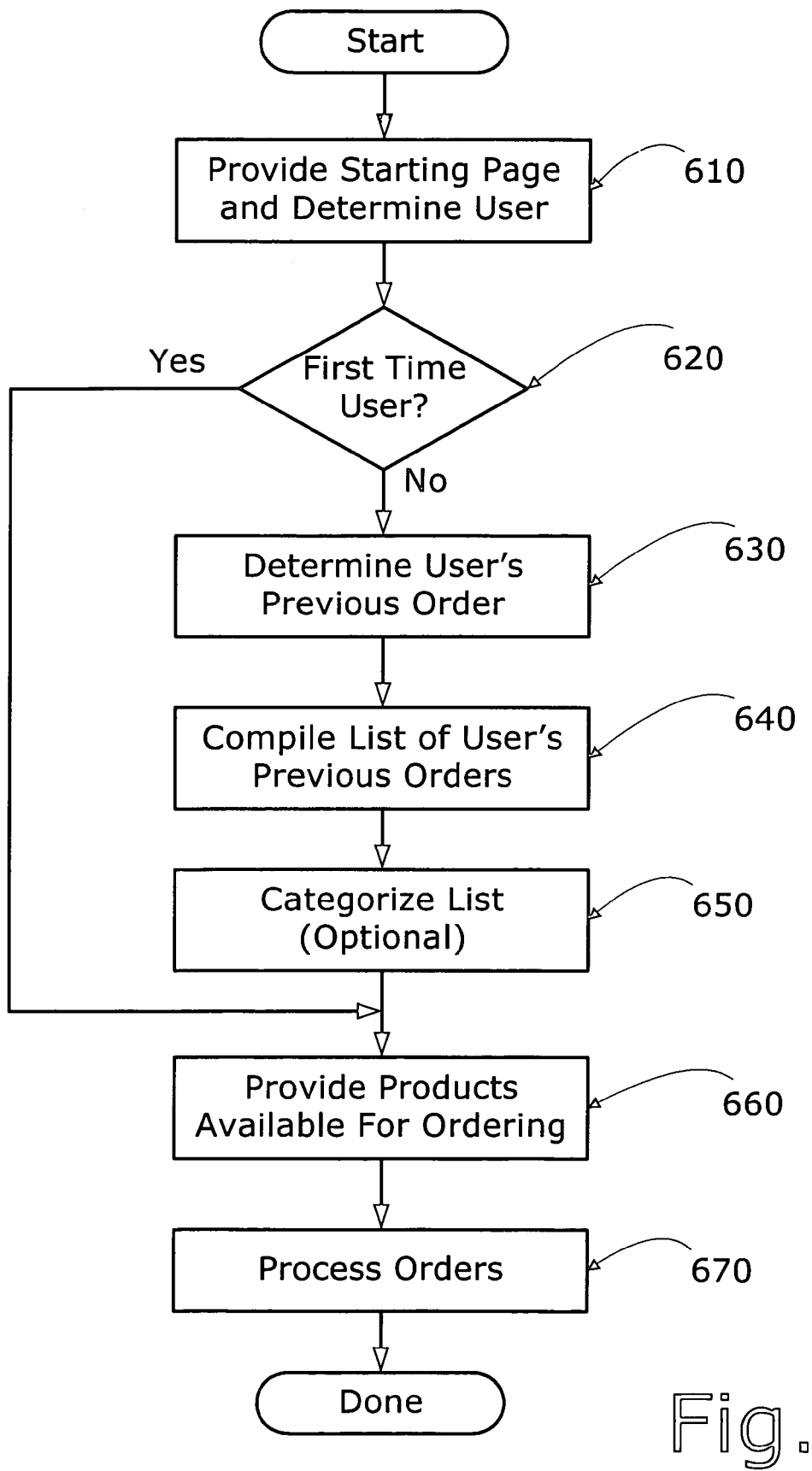
FIG. 6 is a flow diagram on one embodiment of a process for providing a list of previously ordered products.

FIG. 6 is a flow diagram on one embodiment of a process for providing a list of previously ordered products. A server provides a starting page and determines a user at 610. In one embodiment, the user accesses the starting page via a browser application such as, for example, Internet Explorer® available from Microsoft Corporation of Redmond, Wash., or Navigator® available from Netscape Communications of Mountain View, Calif. The identity of the user can be determined by, for example, use of a cookie stored on an electronic system running the browser application, or by a login procedure.

The server determines whether the user is a first-time user at 620. In one embodiment, a cookie is used to determine whether the user is a first-time user. In alternate embodiments, the user can supply a user name and/or password, a card identifying the user, or any other manner of determining the identity of the user. If no information is available indicating whether the user is a first-time user, the user is treated as a first-time user at 620.

If the user is not a first-time user at 620, the user's previous orders are determined at 630. In one embodiment, a user database is maintained to record orders by users as well as other useful information related to the user. In alternate embodiments, the previous purchase information can be stored, for example, by the user's electronic device (e.g., computer system, personal digital assistant, set-top box) running a browser application, or by any other manner.

In one embodiment, the server compiles a list of the user's previous orders at 640. In alternate embodiments, the user's electronic device or another electronic device can be used to compile the list of previous orders. In one embodiment, the list is compiled as an HTML document; however, other document types can also be used.

In one embodiment, the list is categorized at 650; however, categorization of the list is optional. The list can be categorized by date, type of product ordered, products currently searched for, or in any other appropriate manner.

The products available for ordering are provided at 660. If the user is a first-time user at 620, the list compilation (e.g., 630-650) is skipped for that user and the products are presented. If the user is not a first-time user, the list of previously ordered products is also provided with the list, which can be accessible, for example, as a menu or as an HTML link. Any orders made by the user are processed at 670.

In one embodiment, the list of products previously purchased is analyzed for repeat purchases. Information related to repeat purchases (e.g., the number of times ordered, other comparable products/formats) can be presented to the user. In one embodiment, the frequency of purchases are tracked for one or more products for a user.

When the time for reorder is near, a reminder (e.g., an electronic mail message) can be sent to the user to remind the user to reorder the product. In one embodiment, server 360 sends the reminder; however, any device can be used to track products and send reminders. Tracking of purchase patterns with or without reminder messages can be provided for both prescription and non-prescription products. For use with a prescription product, the user can be allowed to authorize a refill of the prescription by responding to the reminder so that the prescription is filled and ready for the user when the previously purchased product is depleted.

Generating Product Feedback

Figure 7:
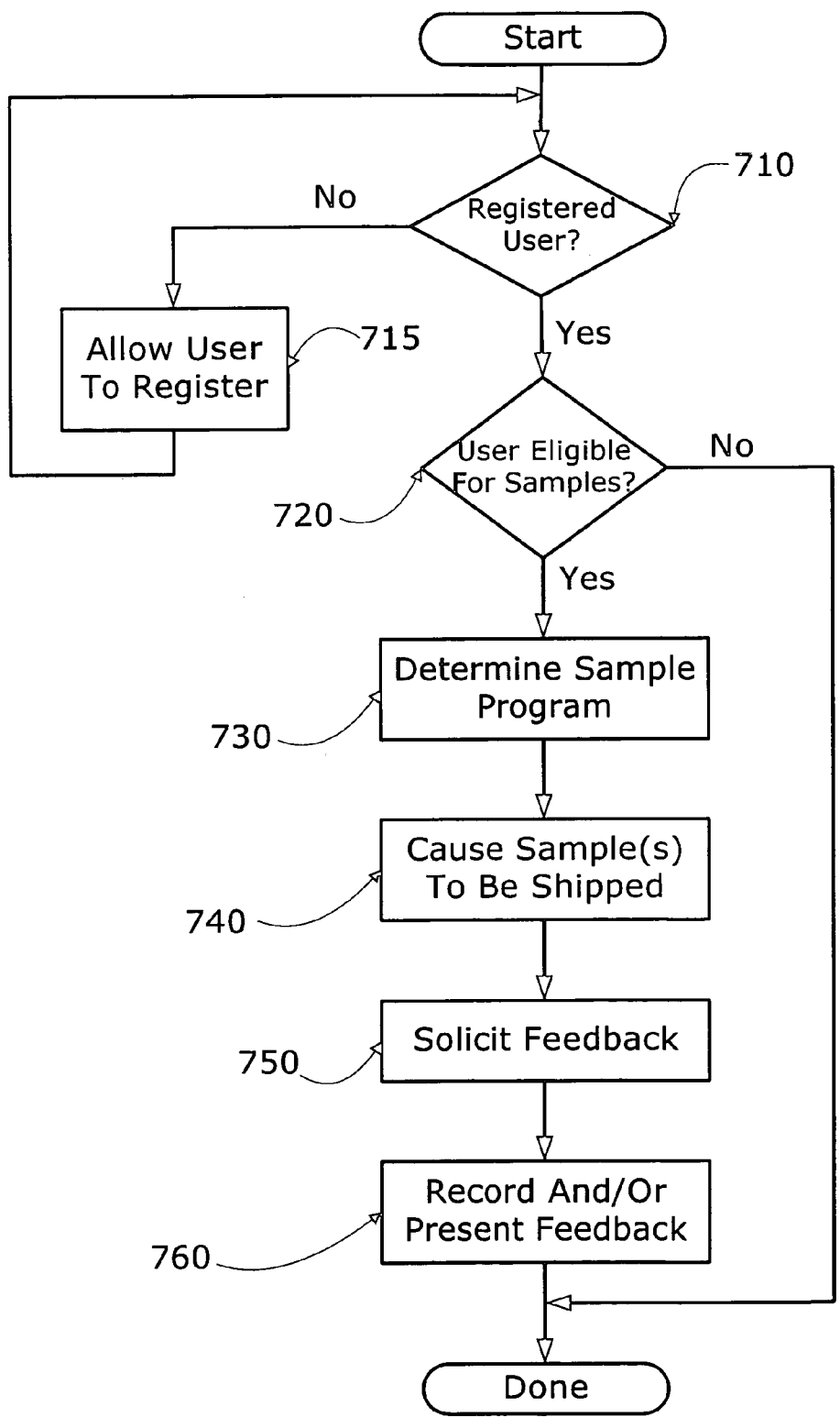
FIG. 7 is a flow diagram of one embodiment of a process for generating product feedback.

FIG. 7 is a flow diagram of one embodiment of a process for generating product feedback. In one embodiment, the process of FIG. 7 is performed by a server device that also provides an electronic commerce Web site; however, the process can be performed by other devices, for example, an electronic device coupled to the server that provides the electronic commerce Web site.

The server determines whether a user is a registered user at 710. Requiring a user to be a registered user is not necessary; however, requiring the user to be a registered user allows the process of FIG. 7 to be performed in a more transparent manner to the user and allows more efficient tracking of feedback. If the user is not a registered user at 710, the user is allowed to register at 715 to be eligible to receive samples. To register, a user can provide identifying information (e.g., name, address), demographic information (e.g., gender, age), or other useful information.

If the user is registered at 710, the server determines whether the user is eligible for samples at 720. User eligibility can be determined based on, for example, demographic information, the number of samples of the product previously distributed, the number of samples previously received by the user, the user's history with respect to providing timely feedback, or any other criteria. If the user is not eligible to receive samples at 720, the user is informed that he/she is ineligible to receive samples.

The sample program to be provided to the user is determined at 730. Use of the phrase "sample program" refers to a procedure or process by which products are provided to purchasers or potential purchasers for evaluation purposes. In one embodiment, a user is presented with products available for sampling and can "sign up" or apply for the sampling program. From a group of applicants, users that meet a predetermined profile are selected for the sampling program. For example, server 360 can select users for the sampling program based on predetermined criteria (e.g., age, geographical location, other products purchased).

Various other sampling programs can be implemented based on, for example, the type of product sampled, the user receiving sample, etc. Smaller products (e.g., soap, pencils) can be provided at little or no cost to the user to sample. Larger, more expensive products (e.g., exercise equipment, computer hardware) can be loaned to the user for a predetermined period of time. Multiple sample programs can be applied to a single product based on, for example, the amount of time remaining in a sampling program, the user demographics, etc.

The server causes the sample(s) to be shipped to the selected users at 740. In one embodiment, the server sends a notification to a shipping center indicating one or more products should be shipped to a specific user at a specific address. The notification can be generated and communicated in any appropriate manner. In one embodiment, the notification is electronic mail. In alternate embodiments, an order processing process used for general processing of orders is used.

Feedback is solicited at 750. In one embodiment, a link to a form is automatically sent (e.g., by server 360) by electronic mail a predetermined time period (e.g., 10 days) to users that have received samples. In one embodiment, the feedback is in an electronic form that is electronically mailed to the user receiving the samples. In alternate embodiments, the feedback is an electronic form that is provided by the server that provides the electronic commerce Web page or by another electronic device. The feedback can also be an independent hardcopy of a questionnaire that is shipped with the samples or send to the user independent of the samples. Solicitation of feedback can also include reminder notifications, such as electronic mail messages, that remind the user to provide feedback.

The feedback provided by the user is recorded and/or presented at 760. In one embodiment, all feedback provided by various users is processed to provide the electronic commerce retailer with information related to the product. Complete and/or edited versions of feedback provided by the users can be presented by the electronic commerce Web site so that subsequent users can have access to the feedback provided by the users that received the samples.

In the foregoing specification, the invention has been described with reference to specific embodiments thereof. It will, however, be evident that various modifications and changes can be made thereto without departing from the broader spirit and scope of the invention. The specification and drawings are, accordingly, to be regarded in an illustrative rather than a restrictive sense.

What is claimed is:

1. A method comprising:
   receiving, over a computerized network, a prescription order request from a user, the prescription order including an order for at least one prescription medication and at least one non-prescription medication, wherein the user is an individual, other than a prescribing physician, seeking to fill a prescription written by the prescribing physician, corresponding to the prescription order;
   forwarding, over the computerized network, the prescription order request to a distribution center;
   providing, over the computerized network, to the distribution center prescription data corresponding to the prescription generated prior to the prescription order request;
   generating, electronically, in response to the distribution center acknowledging receipt of prescription data, a pre-fill order to cause the distribution center to fill the prescription prior to a payment for the medication from the user and at least one of a drug utilization review, a substitution review, and an insurance adjudication;
   causing, electronically, as a result of the pre-fill order, an insurance company to provide to the distribution center an amount of the payment,
   receiving, over the computerized network, from the distribution center, an indication of a medication to be used to fill the prescription order and the amount of the payment to be received from the user;
   generating, electronically, a ship order message in response to receiving the payment; and
   shipping, by the distribution center, the medication in response to receiving the ship order message.

2. The method of claim 1 further comprising selecting, electronically, a distribution center based, at least in part, on a shipping address associated with the prescription order and a location of the distribution center.

3. The method of claim 2 wherein the prescription order is electronically divided into at least two sub-orders comprising a first sub-order for at least one prescription medication and a second sub-order for at least on non-prescription medication.

4. The method of claim 3 wherein the first sub-order is sent over the computerized network to a first distribution center and the second sub-order is sent over the computerized network to a second distribution center.

5. A machine-readable medium having stored thereon sequences of instruction to implement a World Wide Web site, the sequence of instructions, when executed by one or more processors, cause one or more electronic systems to:
   receive a prescription order request from a user via a World Wide Web site wherein the prescription order includes an order for at least one prescription medication and at least one non-prescription medication, the user being an individual, other than a prescribing physician, seeking to fill a prescription written by the prescribing physician, corresponding to the prescription order;
   forward the prescription order request to a distribution center;
   provide to the distribution center prescription data corresponding to the prescription generated prior to the prescription order request;
   generate, in response to the distribution center acknowledging receipt of prescription data, a pre-fill order to cause the distribution center to fill the prescription prior to a payment for the medication from the user and at least one of a drug utilization review, a substitution review, and an insurance adjudication;
   cause, as a result of the pre-fill order, an insurance company to provide to the distribution center an amount of the payment;
   receive, from the distribution center, an indication of a medication to be used to fill the prescription order and the amount of the payment to be received from the user;
   generate, a ship order message in response to receiving the payment; and
   ship, by the distribution center, the medication in response to receiving the ship order message.

6. The machine-readable medium of claim 5 further comprising sequences of instructions that, when executed by the one or more processors, cause the one or more electronic systems to select a distribution center based, at least in part, on a shipping address associated with the prescription order and a location of the distribution center.

7. The machine-readable medium of claim 6 wherein the prescription order is divided into at least two sub-orders comprising a first sub-order for at least one prescription medication and a second sub-order for at least one non-prescription medication.

8. The machine-readable medium of claim 7 wherein the first sub-order is sent to a first distribution center and the second sub-order is sent to second distribution center.

9. An apparatus comprising:
   means for receiving, over a computerized network, a prescription order request from a user via a World Wide Web site, the prescription order including an order for at least one prescription medication and at least one non-prescription medication, wherein the user is an individual, other than a prescribing physician, seeking to fill a prescription written by the prescribing physician, corresponding to the prescription order;
   means for receiving, over the computerized network, a prescription order request from a user via a World Wide Web site;
   means for forwarding, over the computerized network, the prescription order request to a distribution center;
   means for providing to the distribution center, over the computerized network, prescription data corresponding to the prescription generated prior to the prescription order request;
   means for electronically generating, in response to the distribution center acknowledging receipt of prescription data, a pre-fill order to cause the distribution center to fill the prescription prior to a payment for the medication from the user and at least one of a drug utilization review, a substitution review, and an insurance adjudication;

means for electronically causing, as a result of the pre-fill order, an insurance company to provide to the distribution center an amount of the payment;

means for receiving, over the computerized network, from the distribution center, an indication of a medication to be used to fill the prescription order and the amount of the payment to be received from the user;

means for electronically generating a ship order message in response to receiving the payment; and means for shipping, by the distribution center, the medication in response to receiving the ship order message.

10. The apparatus of claim 9 further comprising means for electronically selecting a distribution center based, at least in part, on a shipping address associated with the prescription order and a location of the distribution center.

11. The apparatus of claim 10 wherein the prescription order is electronically divided into at least two sub-orders comprising a first sub-order for at least one prescription medication and a second sub-order for at least one non-prescription medication.

12. The apparatus of claim 11 wherein the first sub-order is sent over the computerized network to a first distribution center and the second sub-order is sent over the computerized network to a second distribution center.

13. A network comprising:
a World Wide Web server to provide a World Wide Web site to receive prescription order requests, received from an individual, other than a prescribing prescription, seeking to fill a prescription, corresponding to the prescription order request, written by the prescribing physician, wherein the prescription order includes an order for at least one prescription medication and at least one non-prescription medication;

a data store coupled to the World Wide Web server to receive prescription order requests from the World Wide Web server;

a server coupled to the data store, the server to retrieve prescription order requests from the data store and to forward the prescription order requests to a distribution center;

wherein the one or more servers
sends the prescription order requests to the distribution center to fill prescriptions corresponding to the prescription order requests in response to the distribution center acknowledging receipt of prescription data corresponding to the prescription generated prior to the prescription order request, and generates a pre-fill order causing the distribution center to fill the prescription prior to a payment for the medication from the user and at least one of a drug utilization review, a substitution review, and an insurance adjudication, causing an insurance company to provide to the distribution center an amount of the payment, receiving, from the distribution center, an indication of a medication to be used to fill the prescription order and the amount of the payment to be received form the user and further wherein the server generates a ship order message in response to receiving the payment to cause a distribution center to ship the medication.

14. The network of claim 13 wherein the server selects the distribution center from a set of one or more distribution centers based, at least in part, on a shipping address associated with the prescription order and a location of the distribution center.

15. The network of claim 14 wherein the prescription order is divided into at least two sub-orders comprising a first sub-order for at least one prescription medication and a second sub-order for at least one non-prescription medication.

16. The method of claim 15 wherein the first sub-order is sent to a first distribution center and the second sub-order is sent to a second distribution center.

* * * * *